US009216050B2

(12) United States Patent
Condie et al.

(10) Patent No.: US 9,216,050 B2
(45) Date of Patent: Dec. 22, 2015

(54) DETECTION OF MICROBUBBLE FORMATION DURING CATHETER ABLATION

(75) Inventors: Catherine R. Condie, Shoreview, MN (US); Marshall L. Sherman, Cardiff by the Sea, CA (US); Mark T. Stewart, Lino Lakes, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 525 days.

(21) Appl. No.: 13/460,864

(22) Filed: May 1, 2012

(65) Prior Publication Data

US 2013/0296839 A1 Nov. 7, 2013

(51) Int. Cl.
  *A61B 18/12* (2006.01)
  *A61B 18/00* (2006.01)
  *A61B 18/14* (2006.01)

(52) U.S. Cl.
  CPC ......... *A61B 18/1206* (2013.01); *A61B 18/1492* (2013.01); *A61B 2018/00267* (2013.01); *A61B 2018/00577* (2013.01); *A61B 2018/00642* (2013.01); *A61B 2018/00666* (2013.01); *A61B 2018/00678* (2013.01); *A61B 2018/00702* (2013.01); *A61B 2018/00708* (2013.01); *A61B 2018/00779* (2013.01); *A61B 2018/00875* (2013.01); *A61B 2018/00898* (2013.01)

(58) Field of Classification Search
  USPC ............................. 606/38, 32, 34, 41, 45–52
  See application file for complete search history.

(56) References Cited

U.S. PATENT DOCUMENTS

| 5,514,129 | A | 5/1996 | Smith |
| 5,681,308 | A | 10/1997 | Edwards et al. |
| 5,769,846 | A | 6/1998 | Edwards et al. |
| 5,897,577 | A | 4/1999 | Cinbis et al. |
| 6,050,267 | A | 4/2000 | Nardella et al. |
| 6,132,426 | A | 10/2000 | Kroll |
| 6,203,541 | B1 | 3/2001 | Keppel |
| 6,217,574 | B1 | 4/2001 | Webster |
| 6,256,540 | B1 | 7/2001 | Panescu et al. |
| 6,391,024 | B1 | 5/2002 | Sun et al. |
| 6,546,270 | B1 | 4/2003 | Goldin et al. |
| 6,730,079 | B2 | 5/2004 | Lovewell |
| 7,736,357 | B2 | 6/2010 | Lee, Jr. et al. |
| 8,398,626 | B2 * | 3/2013 | Buysse et al. ................... 606/34 |

(Continued)

FOREIGN PATENT DOCUMENTS

| EP | 1151725 A1 | 11/2001 |
| EP | 1429678 B1 | 3/2006 |

(Continued)

*Primary Examiner* — Paula J Stice
(74) *Attorney, Agent, or Firm* — Christopher & Weisberg, P.A.

(57) ABSTRACT

A method and system for detecting microbubble formation during a radiofrequency ablation procedure. The method includes measuring an impedance of a pair of electrodes, at least one electrode in the pair of electrodes being coupled to a treatment assembly of a medical device. Radiofrequency ablation energy is transmitted between the pair of electrodes. The transmission of radiofrequency ablation energy between the pair of electrodes is terminated when after a predetermined period of time the measured impedance in either of the electrodes in the pair of electrodes is a predetermined percentage above a measured minimum impedance and a measured power is above a predetermined power threshold. An alert is generated indicating at least one of the formation and release of microbubbles proximate the pair of electrodes.

19 Claims, 9 Drawing Sheets

(56) References Cited

U.S. PATENT DOCUMENTS

| | | |
|---|---|---|
| 2002/0032439 A1 | 3/2002 | Hareyama |
| 2004/0064161 A1 | 4/2004 | Gunderson et al. |
| 2005/0222562 A1 | 10/2005 | Lovewell |
| 2005/0283074 A1 | 12/2005 | Jackson et al. |
| 2007/0062547 A1 | 3/2007 | Pappone |
| 2007/0173808 A1 | 7/2007 | Goble |
| 2008/0281312 A1 | 11/2008 | Werneth et al. |
| 2008/0281314 A1 | 11/2008 | Johnson et al. |
| 2009/0030664 A1 | 1/2009 | Bridges et al. |
| 2009/0240244 A1 | 9/2009 | Malis et al. |
| 2009/0275827 A1 | 11/2009 | Aiken et al. |
| 2010/0049188 A1 | 2/2010 | Nelson et al. |
| 2010/0168557 A1 | 7/2010 | Deno et al. |
| 2010/0168571 A1 | 7/2010 | Savery et al. |
| 2010/0179538 A1 | 7/2010 | Podhajsky |
| 2010/0274238 A1 | 10/2010 | Klimovitch |
| 2011/0046618 A1 | 2/2011 | Minar et al. |
| 2011/0130755 A1 | 6/2011 | Bhushan et al. |
| 2011/0144524 A1 | 6/2011 | Fish et al. |
| 2011/0152712 A1 | 6/2011 | Cao et al. |
| 2011/0230876 A1 | 9/2011 | Hong et al. |
| 2011/0270243 A1 | 11/2011 | Skarda et al. |
| 2012/0265194 A1* | 10/2012 | Podhajsky ............... 606/34 |

FOREIGN PATENT DOCUMENTS

| | | |
|---|---|---|
| EP | 1803410 A1 | 7/2007 |
| EP | 1867279 A3 | 12/2007 |
| EP | 1280467 B1 | 11/2008 |
| WO | 2004011090 A2 | 2/2004 |
| WO | 2011103129 A2 | 8/2011 |

* cited by examiner

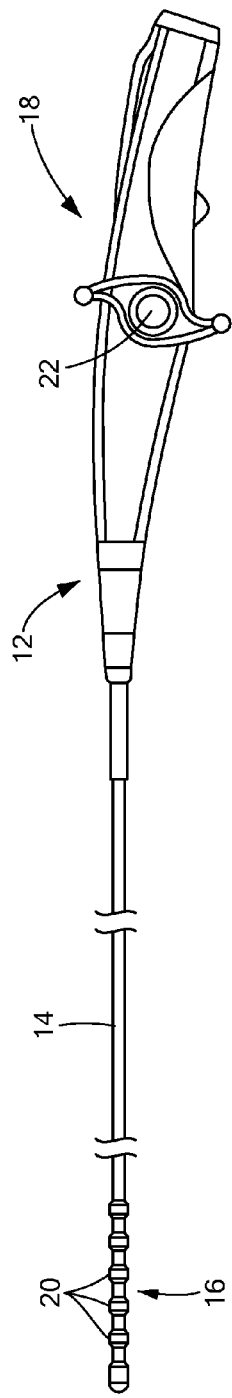
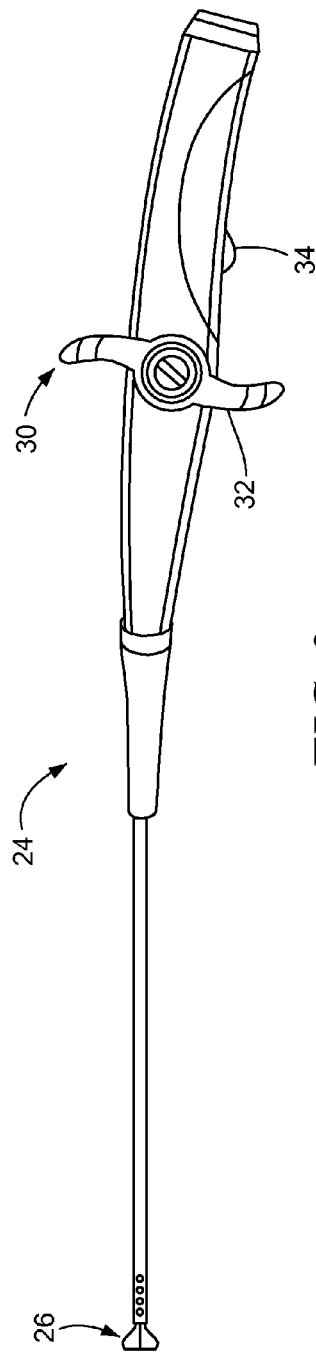
FIG. 2
FIG. 3

DETECTION OF MICROBUBBLE FORMATION DURING CATHETER ABLATION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for detecting microbubbles during an ablation procedure.

BACKGROUND OF THE INVENTION

Current radiofrequency ablation ("RF") devices are constructed in a variety of configurations to target specific maladies and to provide for specific treatment protocols. In particular, many RF ablation devices have one or more treatment regions in which multiple treatment electrodes are disposed and are torqueable, or otherwise manipulatable, into a variety of different geometric configurations to treat particular cardiovascular tissues. For example, treatment electrodes may be coupled to an array or a carrier assembly manipulatable to define substantially linear, helical, and circular configurations depending on the desired treatment to be performed. In such multi-electrode configurations, each adjacent electrode may be spaced a distance away, whether longitudinal or radial, such that that bipolar or unipolar radiofrequency energy may be transmitted between the electrodes to treat the tissue.

Because the treatment electrodes may be manipulated into a variety of different positions, adjacent electrodes may be unintentionally positioned too close to one another such during transmission of radiofrequency energy, microbubbles may be formed around or on the electrodes. For example, when the electrode array is torqued to define a substantially circular configuration, when a distal electrode in the array is torqued and manipulated toward a proximal electrode in the array to define a circle, depending on the skill of the surgeon, the array may be over-manipulated such that two or more electrodes may be sufficiently close to one another to cause bubble formation, but not a short circuit between the electrodes. The presence of a high current density between the closely spaced electrodes causes overheating and production of large volume of bubbles surrounding the electrodes. Current methods of detecting short circuits in electrosurgical devices do not provide any method or mechanism for detecting dangerous bubble formation.

Accordingly, what is needed is a method of a microbubble detection that facilitates the on-off operation of individual electrodes in an electrode array that is specific to a particular energy delivery mode.

SUMMARY OF THE INVENTION

The present invention advantageously provides a method and system for detecting microbubble formation during a radiofrequency ablation procedure. The method includes measuring an impedance of a pair of electrodes, at least one electrode in the pair of electrodes being coupled to a treatment assembly of a medical device. Radiofrequency ablation energy is transmitted between the pair of electrodes. The transmission of radiofrequency ablation energy between the pair of electrodes is terminated when after a predetermined period of time the measured impedance in either of the electrodes in the pair of electrodes is a predetermined percentage above a measured minimum impedance and a measured power is above a predetermined power threshold. An alert is generated indicating at least one of the formation and release of microbubbles proximate the pair of electrodes.

In another embodiment, the system includes a medical device having a treatment assembly, the treatment assembly having a plurality of electrode pairs, the treatment assembly being manipulatable to define a substantially circular geometric configuration. A control unit is included and operable to measure an impedance of a first pair of the plurality of electrode pairs; transmit radiofrequency ablation energy between the plurality of electrode pairs; and terminate the transmission of radiofrequency ablation energy between the pair of electrodes when after a predetermined period of time the measured impedance in either of the electrodes in the pair of electrodes is a predetermined percentage above a measured minimum impedance and a measured power is above a predetermined power threshold. The control unit is further operable to generate an alert indicating at least one of the formation and release of microbubbles proximate the pair of electrodes.

In yet another embodiment, the method includes positioning an electrode array of a medical device proximate a tissue to be treated, the electrode array defining a proximal end and distal end and having a plurality of electrode pairs spanning from the proximal end to the distal end. The electrode array is manipulated to define a substantially circular geometric configuration. An impedance of a first pair of the plurality of electrode pairs is measured, the first pair of the plurality of electrode pairs including the most proximal electrode in the electrode array and the most distal electrode in the electrode array. Radiofrequency ablation energy is transmitted between the plurality of electrode pairs. The transmission of radiofrequency ablation energy between the first pair of the plurality of electrodes is terminated when after a predetermined period of time the measured impedance in either of the electrodes in the first pair of the plurality of electrodes is a predetermined percentage above a measured minimum impedance and a measured power is above a predetermined power threshold. An alert is generated indicating at least one of the formation and release of microbubbles proximate the pair of electrodes.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 is a side view of an exemplary medical device constructed in accordance with the principles of the present invention;

FIG. 3 is a side view of another exemplary medical device constructed in accordance with the principles of the present invention;

DETAILED DESCRIPTION OF THE INVENTION

Figure 1:
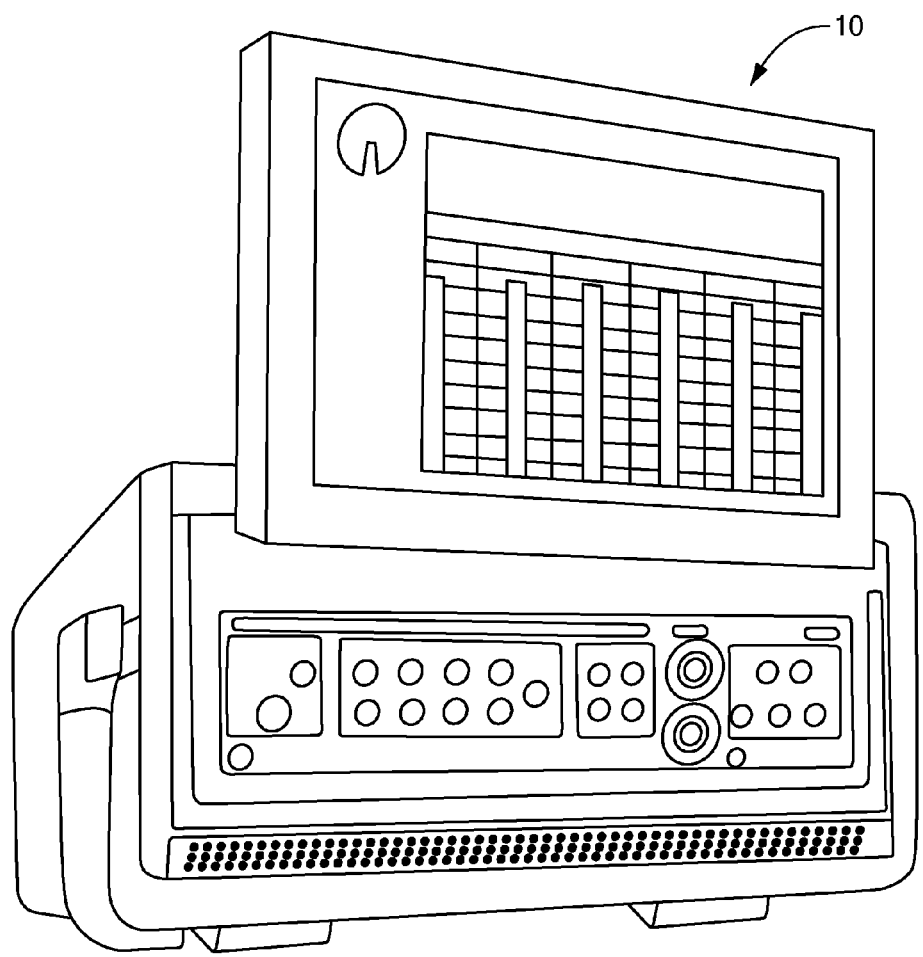
FIG. 1 is a perspective view of an exemplary control unit constructed in accordance with the principles of the present invention.

Referring now to the drawings in which like reference designators refer to like elements, there is shown in FIG. 1 an exemplary embodiment of a control unit such as for example an RF generator constructed in accordance with the principles of the present invention, designated generally as 10. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein may be included in a variety of different combinations or configurations without departing from the scope and spirit of the invention.

The control unit 10 may generally include a display or monitor, operating controls, and couplings for connection to one or more medical devices, one or more patient return or "indifferent" electrodes, an ECG, a power cable, and/or other operating equipment. The control unit 10 may have electronic circuitry to produce the desired ablation energy, to deliver it to the ablation elements of a medical device, to obtain feedback information or parameters from other sensors, and to operate, adjust, modulate or cease providing the ablation energy during a medical treatment of a patient, as well as to display or otherwise inform the physician.

Generally, the control unit 10 may be operated in various modes which may be selected by the physician. For example, ablation energy may be supplied to one or more ablation elements, for example electrodes, in a bipolar mode, a unipolar mode, or a combination bipolar and unipolar mode. A unipolar mode of operation involves delivering energy between one or more ablation elements on a medical device and one or more patient return or reference electrodes touching the skin of the patient or positioned beneath the patient, such as a back plate. A bipolar mode of operation involves delivering energy between at least two electrodes on a medical device. A combination mode of operation involves delivering energy in both bipolar and unipolar modes simultaneously and/or intermittently. When in a combination mode of operation, it may be possible to select various ratios of activity or ablation energy among the bipolar and unipolar modes, including for example ratios such as 1:1, 2:1, or 4:1 (bipolar:unipolar). For example, an energy mode ratio of 4:1 means that four times more bipolar energy is transmitted between a pair of electrodes compared to unipolar energy transmitted.

The medical devices coupled to the control unit 10 may be catheters or surgical probes, including for example an electrophysiology catheter having diagnostic and/or treatment components positionable at or near a target tissue region. For example, the medical device 12 illustrated in FIG. 2 may have a shape and dimensions to reach various treatments sites, such as intraluminal access to vascular anatomy, including for example transseptal access to the left atrium of a patient's heart for subsequent treatment or ablation. The medical device 12 may generally define an elongated, flexible catheter body 14 having a distal treatment assembly 16, as well as a handle assembly 18 at or near a proximal end of the catheter body. The distal treatment assembly 16 may, for example, include one or more ablation elements such as electrodes 20, each of which may be electrically coupled to the control unit 10. The distal treatment assembly 16 of the medical device 12 may have a linear shape, with a plurality of ablation elements or electrodes 20. The catheter body 14 may be both flexible and resilient, with sufficient column strength facilitating steady contact with tissue, which improves signal fidelity in diagnosing contacted tissue as well as improve therapeutic thermal exchange between the device and contacted tissue. The proximal handle assembly 18 has a rotational actuator 22 for manipulating, bending, steering and/or reshaping the distal treatment assembly 16 into various desired shapes, curves, etc.

Figure 4:
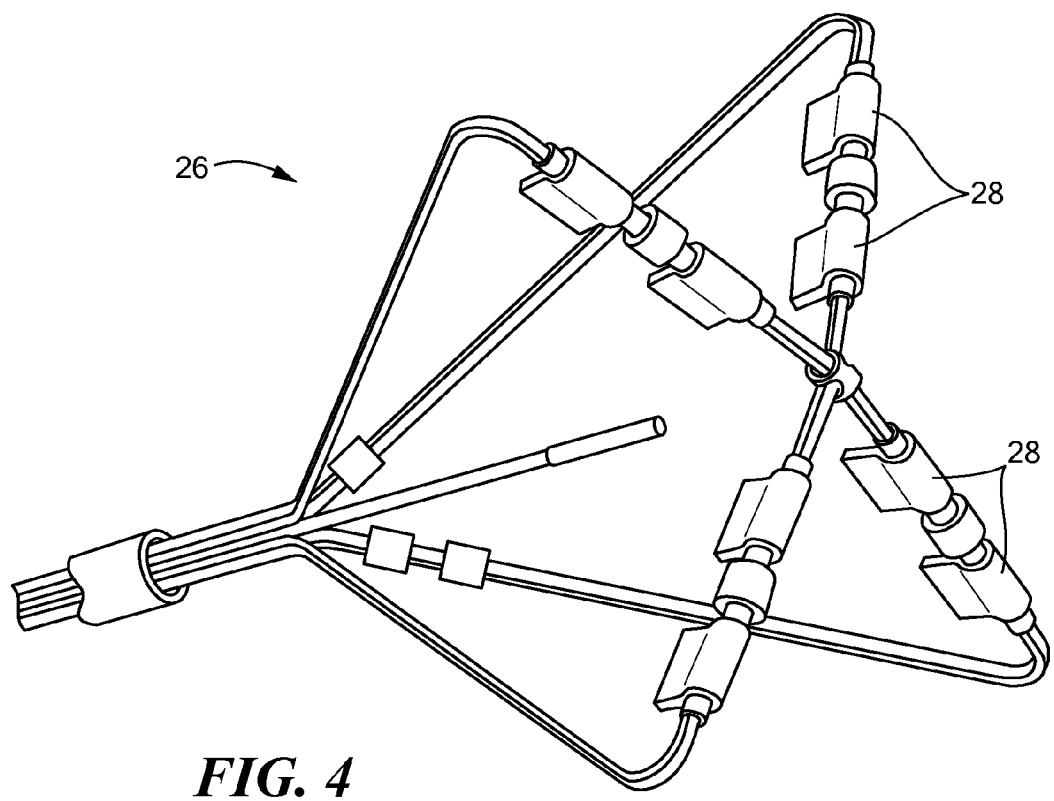
FIG. 4 is a perspective view of an exemplary treatment assembly of a medical device constructed in accordance with the principles of the present invention.
Figure 5:
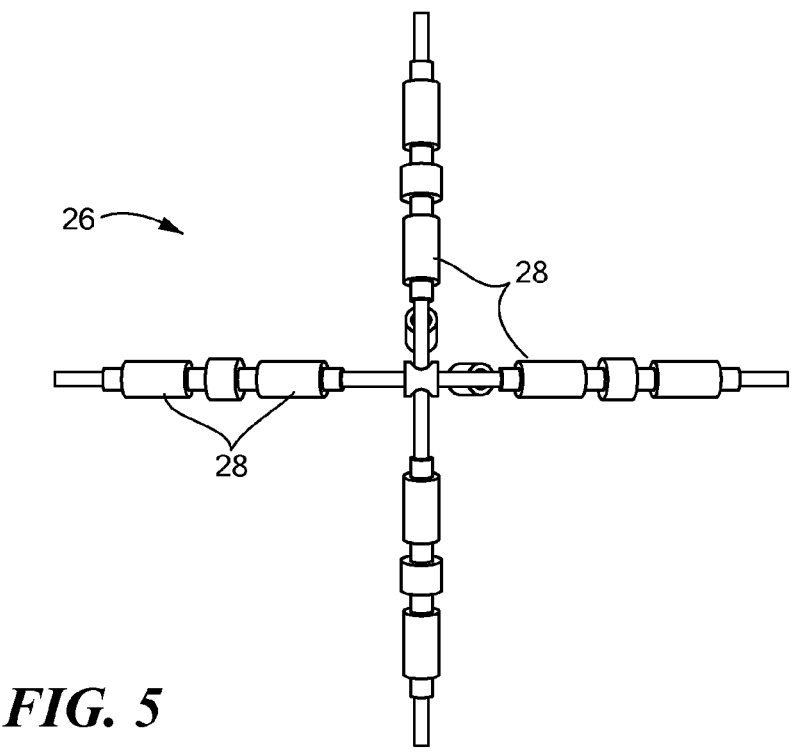
FIG. 5 is a front view of the treatment assembly shown in FIG. 4.

FIGS. 3-5 show a medical device or ablation catheter 24 with a catheter shaft and a distal treatment assembly 26 with compound carrier arms or electrode arrays which may be resilient, so that in a deployed configuration the electrodes 28 have a generally planar arrangement. Similar to the medical device 12 of FIG. 2, the distal treatment assembly 26 may be used for bipolar ablation, unipolar ablation, or a combination thereof. A proximal handle 30 has a rotational actuator 32 for manipulating a distal portion of the ablation catheter, and a linear actuator 34. The linear actuator 32 can advance the distal treatment assembly 26 distally beyond the catheter shaft, and retract the distal treatment assembly 26 proximally inside the catheter shaft. When the distal treatment assembly 26 is advanced distally, it may resiliently expand from a compressed arrangement inside the catheter shaft to the deployed arrangement shown in FIGS. 4 and 5.

Figure 6:
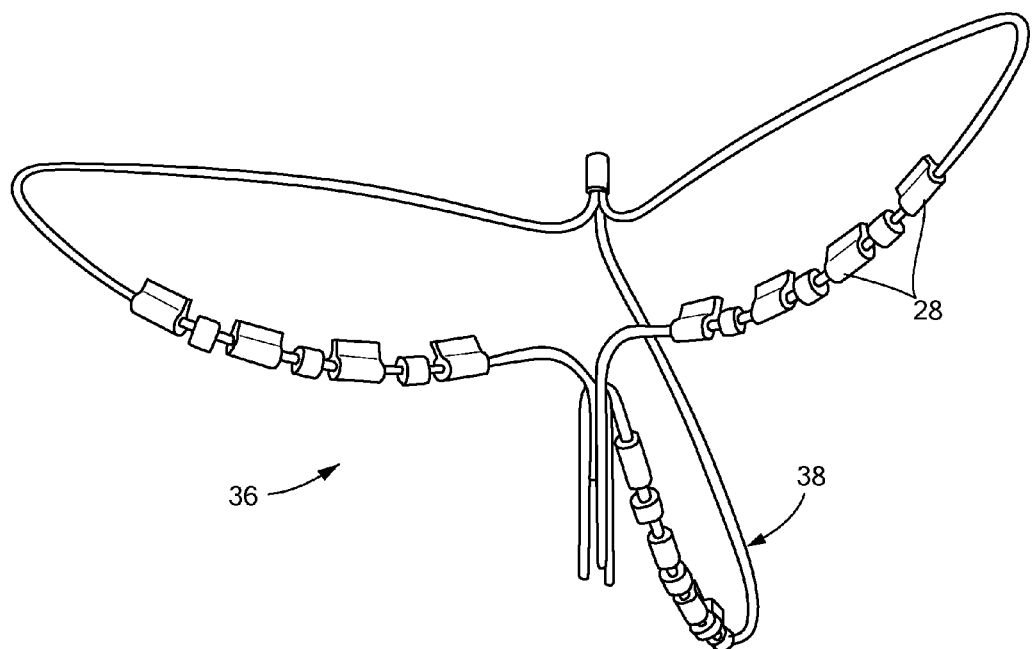
FIG. 6 is a perspective view of the treatment assembly of the medical device shown in FIG. 3.
Figure 7:
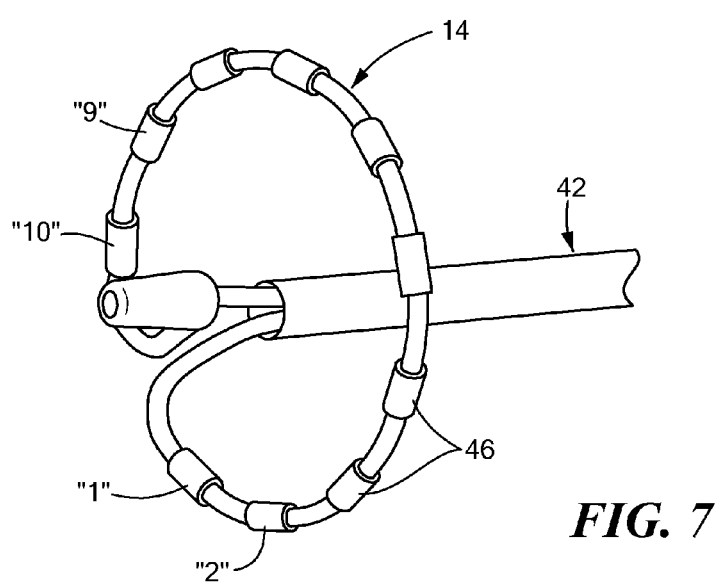
FIG. 7 is a perspective view of another exemplary treatment assembly of a medical device constructed in accordance with the principles of the present invention.

FIG. 6 shows a distal treatment assembly portion of a medical device or catheter 36 which has a resilient framework of carrier arms 38, in which the electrodes 40 have a proximally-directed configuration, which may for example be used for transseptal treatments of a patient's heart. Another distal treatment assembly portion of a medical device or catheter 42 is depicted in FIG. 7, which has a distal electrode array 44 with a plurality of electrodes 46 coupled to the array 44. The distal electrode array 44 may be manipulated to define a substantially linear, helical, or circular configuration, such that linear or substantially circumferential ablation lesion may be created during an ablation procedure.

Figure 8:
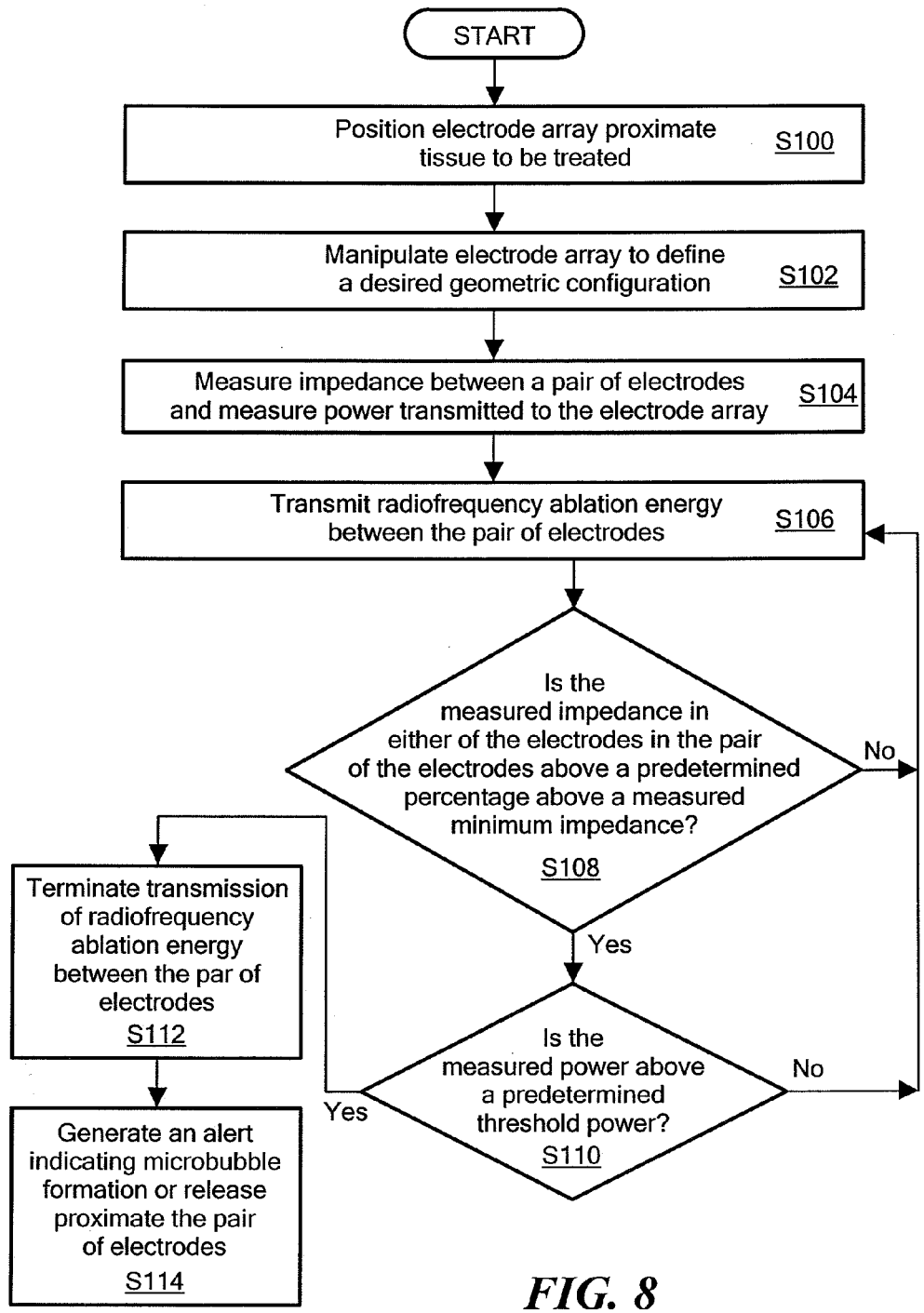
FIG. 8 is a flow chart illustrating an exemplary method of detecting microbubble formation on electrodes.

Now referring to FIG. 8 in which exemplary method of detecting a microbubble formation on a pair of electrodes. The distal treatment assembly 16 of medical device 42, or any electrosurgical catheter, such as the medical devices discussed above, may be navigated through the vasculature toward a desired area of treatment, for example, the pulmonary vein. (Step S100). The treatment assembly may then be manipulated to a desired geometric configuration (Step S102). For example, the medical device 42 may include the electrode array 44, the electrode array 44 being manipulatable to define a substantially linear, helical, or circular configuration. In an exemplary configuration, the electrode array 44 includes ten electrodes 46 spaced a predetermined distance away from each on the array 44. The electrode 46 proximate the proximal end of the electrode array 44 when configured into a substantially linear configuration is referred to herein as electrode "1." The electrode 46 proximate the distal end of the electrode array 44 when configured into a substantially linear configuration is referred to herein as electrode "10." Electrodes 2-9 are disposed between electrodes 1-10, electrode 2 being adjacent electrode 1 and electrode 9 being adjacent electrode 10, and so on. In particular, when the electrode array 44 defines a substantially circular configuration shown in FIG. 7, electrodes 1 and 10 may be substantially radially adjacent each other along the electrode array 44.

Continuing to refer to FIG. 8, an impedance of a pair of the electrodes on the array 44 and/or a pair of electrodes including one electrode on the array 44 and an indifferent or reference electrode (not shown) positioned on the surface of the patient's body, may be measured (S104). In particular, the impedance of electrodes 1 and 10, or 2 and 9, or so on, or every electrode 46 on the array 44, or an electrode 46 and indifferent electrode, may be measured and calculated based on the duty cycle and a preselected power supplied by the control unit 10. In an exemplary calculation, the duty cycle is the voltage. The measured impedance may then be calculated by squaring the voltage and dividing that value by the measured average power. In an exemplary configuration, the measured power may range from between approximately 0-10 W, but may be any power. The measured power, however, may fluctuate as bubbles are either released or formed on the surface of the electrode 46. For example, bubbles on the electrodes 46 may act to insulate the target tissue from the thermal energy transmitted to the tissue, and as a result, the power of the medical device may be automatically increased to increase the amount of energy transmitted to the tissue. Thus, it is contemplated that variations in power and the temperature of the electrodes 46 and/or target tissue may be attributed to bubble release or formation.

To calculate the voltage the duty cycle may be divided by the preset number of fields, for example, 255, to arrive at the percentage of the duty cycle rather than a binary value. The impedance may be measured across all the electrodes 46, some of the electrodes 46, or particular pairs of electrodes depending on the particular geometric configuration defined for the particular ablation treatment.

Radiofrequency ablation energy may be transmitted between two or more of the electrodes 46 on the array 44, and/or between the electrodes 46 and a reference electrode, or between an electrode on the array 44 and an electrode on another medical device (not shown) for a predetermined period of time at the preselected power (S106). For example, radiofrequency ablation energy may be transmitted between electrodes 1 and 10, and/or 2 and 9, and so on, in unipolar, 1:1, 2:1, 4:1, and/or bipolar energy modes. The impedance in Step S104 may be measured before, during, and/or after radiofrequency ablation energy is transmitted between the electrodes 46. After a predetermined period of ablation time, referred to herein as the ramp-up time, the measured impedance may be compared against a minimum measured impedance value to determine if microbubbles are formed on or proximate the electrodes 46 and are interfering with the pair of electrodes.

Figure 9:
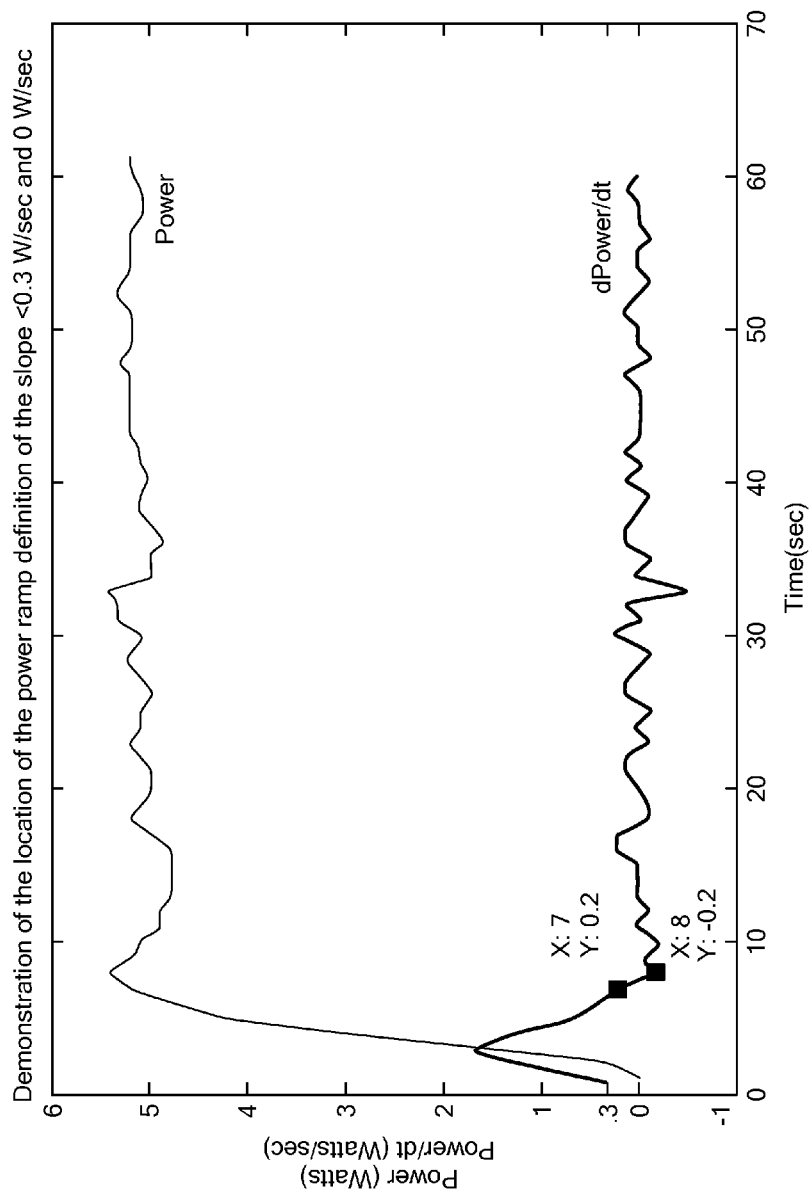
FIG. 9 is a graph showing the measured power over time and the derivative the power with respect to time to determine the ramp-up times.
Figure 10:
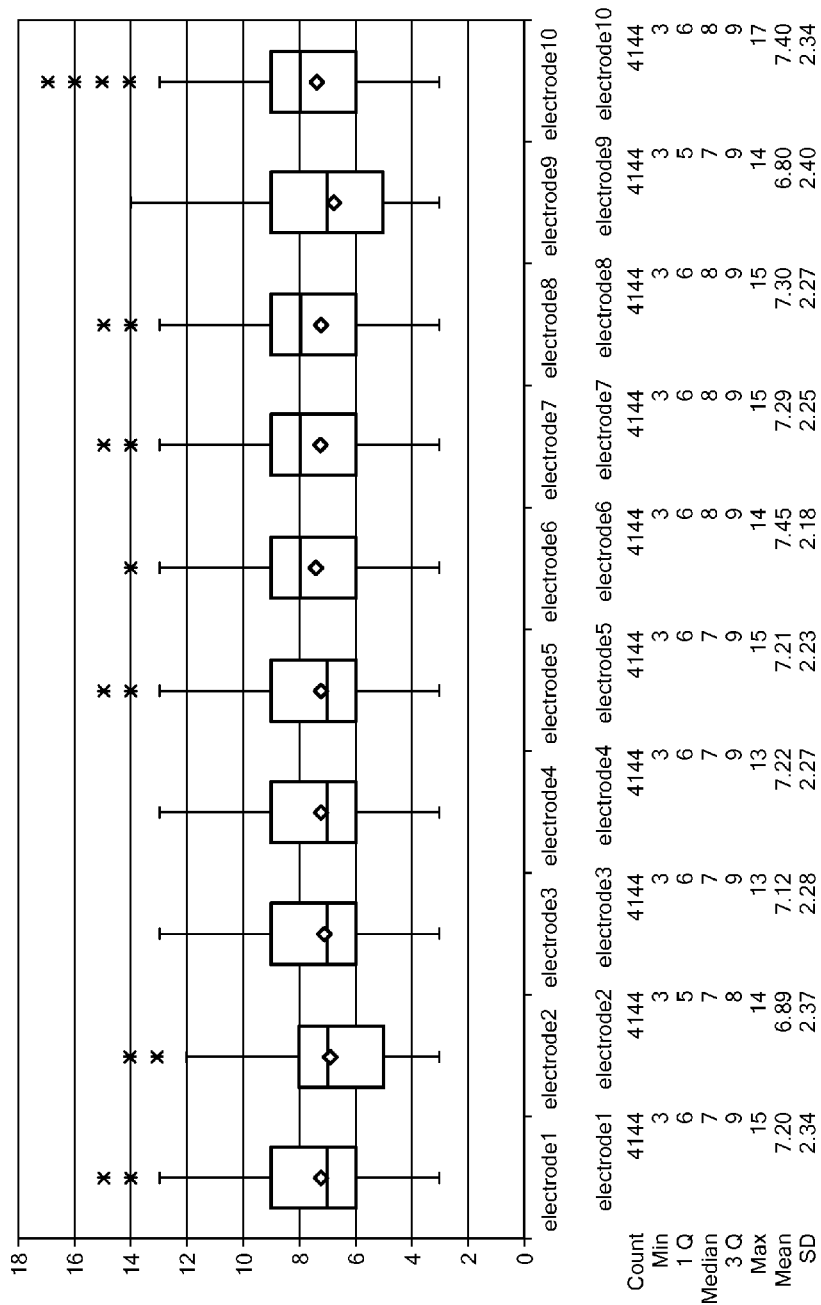
FIG. 10 is a box and whisker plot showing the median time to power plateau in 4144 ablation data sets, per electrode.

In particular, to determine the ramp-up time, an analysis of the ramp-up time on over 4000 ablations was completed. As the temperature reaches a preprogrammed temperature set point, or the power reaches the maximum power, the derivative of the power slows down and eventually crosses zero as seen in the plot in FIG. 9. The time to the derivative<0.3 Watts/second is used as a threshold to determine when the ramp up phase is completed. For example, as shown in FIG. 10, the median value for the ramp-up time is 7 seconds and the quartiles are at 6 and 9 seconds.

When the electrodes 46 are close together but not touching, microbubbles may form on the surface of the electrodes 46 causing the measured impedance to rise above a minimum measured impedance. In particular, the measured impedance, which may fluctuate over time as the target tissue is ablated. Thus the measured minimum impedance may decrease overtime. However, because the electrodes are close together, microbubbles may begin to form or may be instantaneously released, causing the measured impedance to raise from a measured impedance value for a particular energy mode.

Figure 11:
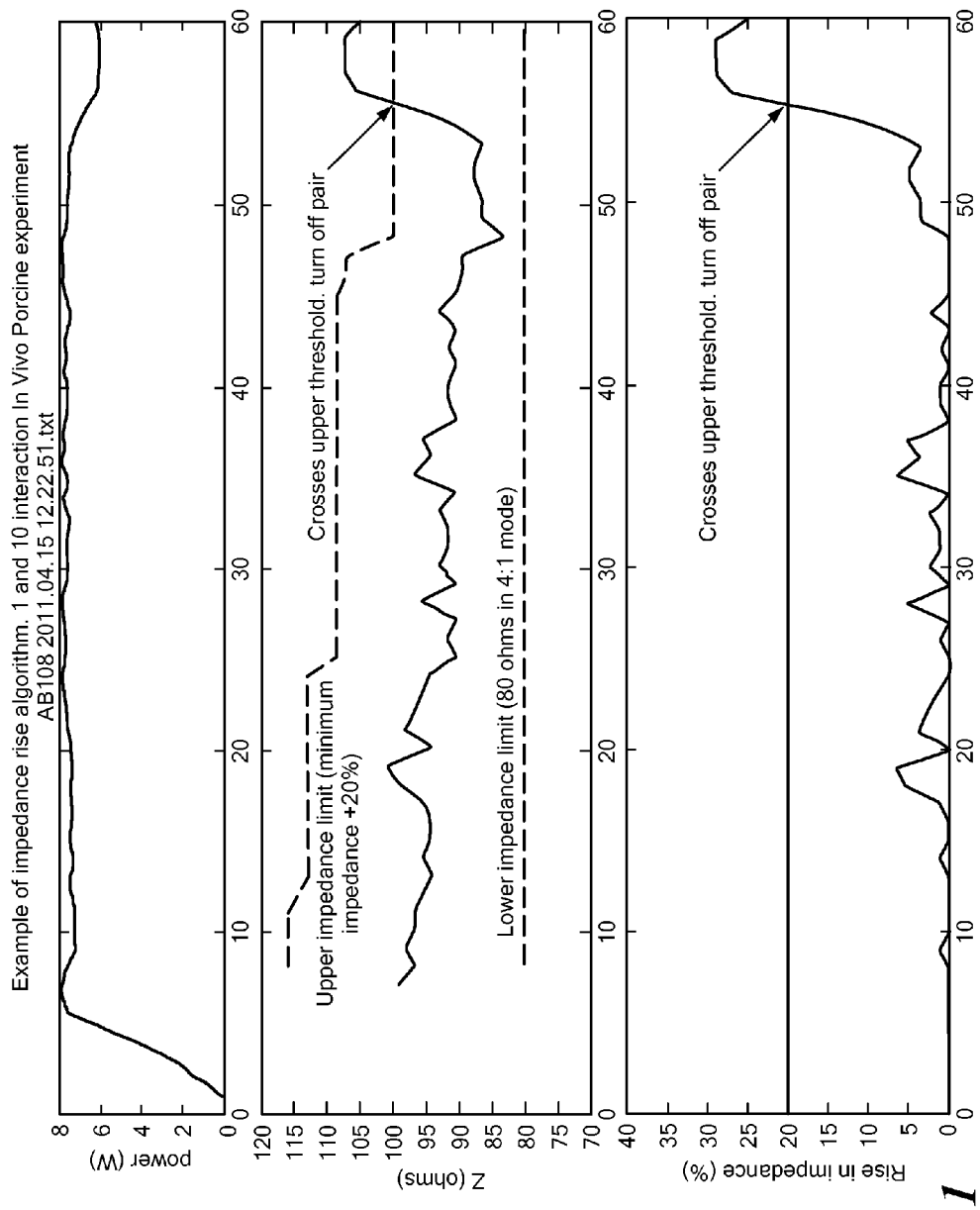
FIG. 11 is graph showing an exemplary ablation procedure with electrodes 1 and 10 in close proximity and exemplary results of a method of detecting microbubble formation.

Now referring to FIG. 11, the impedance at any one of the electrodes 46 or electrode pairs, for example, in electrodes 1 and 10, is measured to determine if the measured impedance is above the minimum measured impedance value for the particular energy mode by a predetermined value or percentage (Step 108). In particular, in the exemplary embodiment shown in FIG. 11 in which radiofrequency ablation energy is transmitted between electrodes 1 and 10 in a 4:1 energy mode, the measured impedances decreases over a period of time as the electrodes 1 and 10 are manipulated and are positioned close to each other. As bubbles are released from surface of electrodes 1 and at approximately 50 seconds, the measured impedance rises sharply, in contrast to bubble formation which occurs over a longer period of time. When the measured impedance rises above a predetermined percentage threshold, for example, 20%, 35%, or any percentage above the minimum measured impedance, or above the present measured impedance, and the measured power is above a predetermined power threshold (Step 110), for example, 2.5 Watts, then the flow of radiofrequency energy to the particular electrode 46 and/or electrode pair may be selectively terminated (Step 112) while the other electrodes 46 in the array 44 may continue to transmit radiofrequency energy. Should the flow of radiofrequency be terminated, the control unit 10 may be operate to generate an alert (Step 114), such as in indicator on the displace, to indicate that microbubbles have either or both been formed on the surface of the electrodes 46 or released from a portion or proximate the electrodes 46 on the array 44. It is further contemplated the measured impedance from an electrode 46 to a reference electrode may be measured independently from the measured impedance between two electrodes 46 on the array 44. In particular the measured impedance values shown in FIG. 11 are combined impedances from both bipolar and unipolar mode measurements. However, the control unit 10 may be operable to separate the impedance measured from unipolar and bipolar mode such that impedance changes owing to bubble formation or release may be attributed to a particular energy ablation mode.

The minimum measured impedance may be a dynamic value or a static value. For example, as shown in FIG. 11, the minimum measured impedance, which may be the lowest measured impedance over time, decrease as the measured impedance decreases. Alternatively, a static minimum impedance threshold may be selected.

Figure 12:
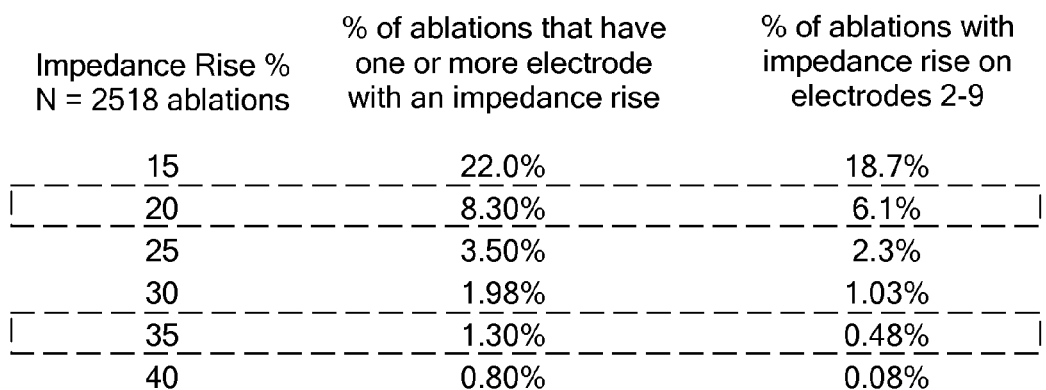
FIG. 12 is a table showing the percentage of ablations in which a percentage of impedance rise was measured in the electrodes.

Alternatively, the transmission of radiofrequency may be terminated to the entire electrode array 44 when the measured impedance rises above the predetermined percentage value. In an exemplary embodiment shown in FIG. 12, when measured impedance rises to approximately 100 ohms from a measured value of approximately 85 ohms, electrodes 1 and 10 are "turned off." In another exemplary embodiment shown in FIG. 12, at a percentage impedance rise threshold of 20%, 8.3% of ablation procedures had at least one instance of an electrode turning off due to an impedance rise. With a threshold of 35%, this percentage decreases to 1.3% of ablations. As such, the microbubble detection algorithm infrequently results in the ablation procedure being affected as the result of microbubble formation at the exemplary percentage thresholds.

The control unit 10 may be programmed to perform the various operations and calculate the measured impedances as discussed above. Specifically, the control unit 10 may automatically terminate to the flow of radiofrequency energy to the electrodes 46 or electrode pairs with measured impedance rise above the predetermined percentage threshold and above a power threshold. Alternatively, the control unit 10 may display a visual warning or emit and audio warning when the measured impedance rises above the percentage threshold such that the operator of the control unit 10 may manually terminate the flow of radiofrequency energy to the affected electrodes 46. Although the method and system described above is described with respect to a distal treatment assembly being configured to define a substantially circular geometric configuration, it is contemplated that the method and system described herein may be used with any configuration of electrodes and distal assemblies in which a shot circuit may occur.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of detecting microbubble formation during a radiofrequency ablation procedure, comprising:
   transmitting radiofrequency ablation energy between a pair of electrodes, at least one electrode in the pair of electrodes being coupled to a treatment assembly of a medical device;
   continuously measuring an impedance between the pair of electrodes;
   continuously measuring a power transmitted to the pair of electrodes by the control unit;
   comparing a measured power to a predetermined power threshold;
   comparing, at between approximately six seconds and approximately nine seconds from the beginning of transmission of radiofrequency ablation energy, a measured impedance to a measured minimum impedance;
   terminating the transmission of radiofrequency ablation energy between the pair of electrodes when:
      the measured impedance in either of the electrodes in the pair of electrodes is a predetermined percentage above the measured minimum impedance; and
      the measured power is above a predetermined power threshold; and
   generating an alert indicating at least one of the formation and release of microbubbles proximate the pair of electrodes based on the comparisons.

2. The method of claim 1, further including transmitting radiofrequency energy between at least one of the electrodes in the pair of electrodes and a reference electrode.

3. The method of claim 1, further including correlating a rise in the measured impedance above a predetermined percentage above the measured minimum impedance to a determination of a presence of bubbles proximate the electrodes.

4. The method of claim 1, wherein the predetermined power threshold is 2.5 Watts.

5. The method of claim 1, wherein the treatment assembly is manipulatable to define a substantially circular geometric configuration, and wherein the pair of electrodes is adjacent each other along the treatment assembly when the treatment assembly defines a substantially circular geometric configuration.

6. The method of claim 1, wherein the predetermined percentage is 20%.

7. The method of claim 1, wherein the predetermined percentage is 35%.

8. A medical system, comprising:
   a medical device having a treatment assembly, the treatment assembly having a plurality of electrode pairs, the treatment assembly being manipulatable to define a substantially circular geometric configuration;
   a control unit operable to:
      transmit radiofrequency ablation energy between the plurality of electrode pairs;
      continuously measure an impedance between a first pair of the plurality of electrode pairs and determine a measured minimum impedance;
      continuously measure a power transmitted to the plurality of electrodes by the control unit;
      compare a measured power to a predetermined power threshold;
      compare, at between approximately six seconds and approximately nine seconds from the beginning of transmission of the radiofrequency ablation energy, a measured impedance to the measured minimum impedance;
      terminate the transmission of radiofrequency ablation energy between the pair of electrodes when:
         the measured impedance in either of the electrodes in the pair of electrodes is a predetermined percentage above the measured minimum impedance; and
         a measured power is above the predetermined power threshold; and
      generate an alert indicating at least one of the formation and release of microbubbles proximate the pair of electrodes based on the comparisons.

9. The system of claim 8, wherein the comparison of the measured impedance to the measured minimum impedance is made at seven seconds from the beginning of transmission of radiofrequency energy.

10. The system of claim 8, wherein the control unit is further operable to transmit radiofrequency energy between at least one of the electrodes in the pair of electrodes and a reference electrode.

11. The system of claim 8, wherein the control unit is further operable to correlate a rise in the measured impedance above a predetermined percentage above the measured minimum impedance to a determination of a presence of bubbles proximate the electrodes.

12. The system of claim 8, wherein the termination of the transmission of radiofrequency ablation energy between the first pair of the plurality of electrode pairs is independent of the transmission of radiofrequency ablation energy between electrode pairs on the electrodes array other than the first pair of the plurality of electrode pairs.

13. The system of claim 8, wherein the predetermined percentage is 20%.

14. The system of claim 8, wherein the predetermined percentage is 35%.

15. The system of claim 8, wherein the predetermined power threshold is 2.5 Watts.

16. A method of detecting microbubble formation during a radiofrequency ablation procedure, comprising:

positioning an electrode array of a medical device proximate a tissue to be treated, the electrode array defining a proximal end and distal end and having a plurality of electrode pairs spanning from the proximal end to the distal end;

manipulating the electrode array to define a substantially circular geometric configuration;

transmitting radiofrequency ablation energy between the plurality of electrode pairs;

continuously measuring an impedance of a first pair of the plurality of electrode pairs, the first pair of the plurality of electrode pairs including the most proximal electrode in the electrode array and the most distal electrode in the electrode array;

continuously measuring a power transmitted to the first pair of the plurality of electrode pairs;

comparing a measured power to a predetermined power threshold;

comparing, at between approximately six seconds and approximately nine seconds from the beginning of the transmission of the radiofrequency ablation energy, a measured impedance to a measured minimum impedance;

terminating the transmission of radiofrequency ablation energy between the first pair of the plurality of electrodes when:

the measured impedance in either of the electrodes in the first pair of the plurality of electrodes is a predetermined percentage above a measured minimum impedance; and a measured power is above a predetermined power threshold; and generating an alert indicating at least one of the formation and release of microbubbles proximate the first pair of the plurality of electrodes based on the comparisons.

17. The method of claim 16, wherein the comparison of the measured impedance to the measured minimum impedance is made at seven seconds from the being nine of transmission of radiofrequency energy.

18. The method of claim 16, wherein the predetermined percentage is 35%.

19. The method of claim 16, wherein the predetermined power threshold is 2.5 Watts.

* * * * *